(12) United States Patent
Thompson et al.

(10) Patent No.: US 6,790,187 B2
(45) Date of Patent: Sep. 14, 2004

(54) SYSTEMS AND METHODS FOR APPLYING ULTRASONIC ENERGY

(75) Inventors: Todd A Thompson, San Jose, CA (US); Veijo Suorsa, Sunnyvale, CA (US); Michael J Howzewski, San Jose, CA (US)

(73) Assignee: TIMI 3 Systems, Inc., Santa Clara, CA (US)

( * ) Notice: Subject to any disclaimer, the term of this patent is extended or adjusted under 35 U.S.C. 154(b) by 463 days.

(21) Appl. No.: 09/938,308

(22) Filed: Aug. 23, 2001

(65) Prior Publication Data
US 2002/0055693 A1 May 9, 2002

Related U.S. Application Data

(63) Continuation-in-part of application No. 09/645,662, filed on Aug. 24, 2000.

(51) Int. Cl.[7] .................................................. A61N 7/00
(52) U.S. Cl. ........................................ 601/2; 600/459
(58) Field of Search ............................. 600/437, 439, 600/459; 601/2–4

(56) References Cited

U.S. PATENT DOCUMENTS

| | | | |
|---|---|---|---|
| 5,520,612 A | 5/1996 | Winder et al. | |
| 5,556,372 A | 9/1996 | Talish et al. | |
| 5,698,531 A | 12/1997 | Nabel et al. | |
| 5,762,616 A | 6/1998 | Talish | |
| 6,126,619 A | 10/2000 | Peterson et al. | |
| 6,200,259 B1 | 3/2001 | March | |
| 6,254,573 B1 | 7/2001 | Haim et al. | |
| 6,261,537 B1 | 7/2001 | Klaveness et al. | |
| 6,273,864 B1 | 8/2001 | Duarte et al. | |

*Primary Examiner*—Ruth S. Smith
(74) *Attorney, Agent, or Firm*—Ryan Kromholz & Manion, S.C.

(57) ABSTRACT

Systems and methods for applying ultrasound energy to a body region. The systems and methods provide an ultrasound applicator including a housing, an ultrasound transducer carried by the housing, and a chamber sized to hold an acoustic coupling media subject to a pressure in acoustic communication with the ultrasound transducer. The systems and methods generate electrical signals to operate the ultrasound transducer to output acoustic energy at a selected intensity level. The systems and methods sense at least one system parameter and compare the sensed system parameter to a desired level. The systems and methods vary the pressure in the chamber based, at least in part, upon the comparison.

14 Claims, 14 Drawing Sheets

SYSTEMS AND METHODS FOR APPLYING ULTRASONIC ENERGY

RELATED APPLICATION

This application is a continuation-in-part of U.S. patent application Ser. No. 09/645,662, filed Aug. 24, 2000, and entitled "Systems and Methods for Enhancing Blood Perfusion Using Ultrasound Energy," which is incorporated herein by reference.

FIELD OF THE INVENTION

This invention relates to systems and methods for increasing blood perfusion, e.g., in the treatment of myocardial infarction, strokes, and vascular diseases.

BACKGROUND OF THE INVENTION

High frequency (5 mHz to 7 mHz) ultrasound has been widely used for diagnostic purposes. Potential therapeutic uses for ultrasound have also been more recently suggested. For example, it has been suggested that high power, lower frequency ultrasound can be focused upon a blood clot to cause it to break apart and dissolve. The interaction between lower frequency ultrasound in the presence of a thrombolytic agent has also been observed to assist in the breakdown or dissolution of thrombi. The effects of ultrasound upon enhanced blood perfusion have also been observed.

While the therapeutic potential of these uses for ultrasound has been recognized, their clinical promise has yet to be fully realized. Treatment modalities that can apply ultrasound in a therapeutic way are designed with the premise that they will be operated by trained medical personnel in a conventional fixed-site medical setting. They assume the presence of trained medical personnel in a non-mobile environment, where electrical service is always available. Still, people typically experience the effects of impaired blood perfusion suddenly in public and private settings. These people in need must be transported from the public or private settings to the fixed-site medical facility before ultrasonic treatment modalities can begin. Treatment time (which is often critical in the early stages of impaired blood perfusion) is lost as transportation occurs. Even within the fixed-site medical facility, people undergoing treatment need to be moved from one care unit to another. Ultrasonic treatment modalities must be suspended while the person is moved.

SUMMARY OF THE INVENTION

The invention provides systems and methods for applying ultrasound energy to a body region. The systems and methods provide an ultrasound applicator including a housing, an ultrasound transducer carried by the housing, and a chamber sized to hold an acoustic coupling media subject to a pressure in acoustic communication with the ultrasound transducer. The systems and methods generate electrical signals to operate the ultrasound transducer to output acoustic energy at a selected intensity level. The systems and methods sense at least one system parameter and compare the sensed system parameter to a desired level. The systems and methods vary the pressure in the chamber based, at least in part, upon the comparison.

In one embodiment, the system parameter includes impedance. In this arrangement, the systems and methods can vary pressure in the chamber based, at least in part, upon variance between the sensed impedance and a desired impedance level.

In one embodiment, the systems and methods select the desired level based upon the selected intensity level.

In one embodiment, the systems and methods vary pressure in the chamber to maintain an essentially constant acoustic output.

In one embodiment, the acoustic coupling media within the chamber conducts heat from the ultrasound transducer.

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with the therapeutic indication of providing increased blood perfusion by the transcutaneous application of ultrasonic energy. That is because the features and advantages of the invention are well suited to this therapeutic indication. Still, it should be appreciated that many aspects of the invention can be applied to achieve other diagnostic or therapeutic objectives as well.

Furthermore, in describing the various aspects of the invention in the context of the illustrated embodiment, the region targeted for an increase in blood perfusion is the thoracic cavity (i.e., the space where the heart and lungs are contained). It should be appreciated, however, that the features of invention have application in other regions of the body, too, for example, in the arms, legs, or brain.

I. System for Providing Noninvasive Ultrasound-Assisted Blood Perfusion

Figure 1:
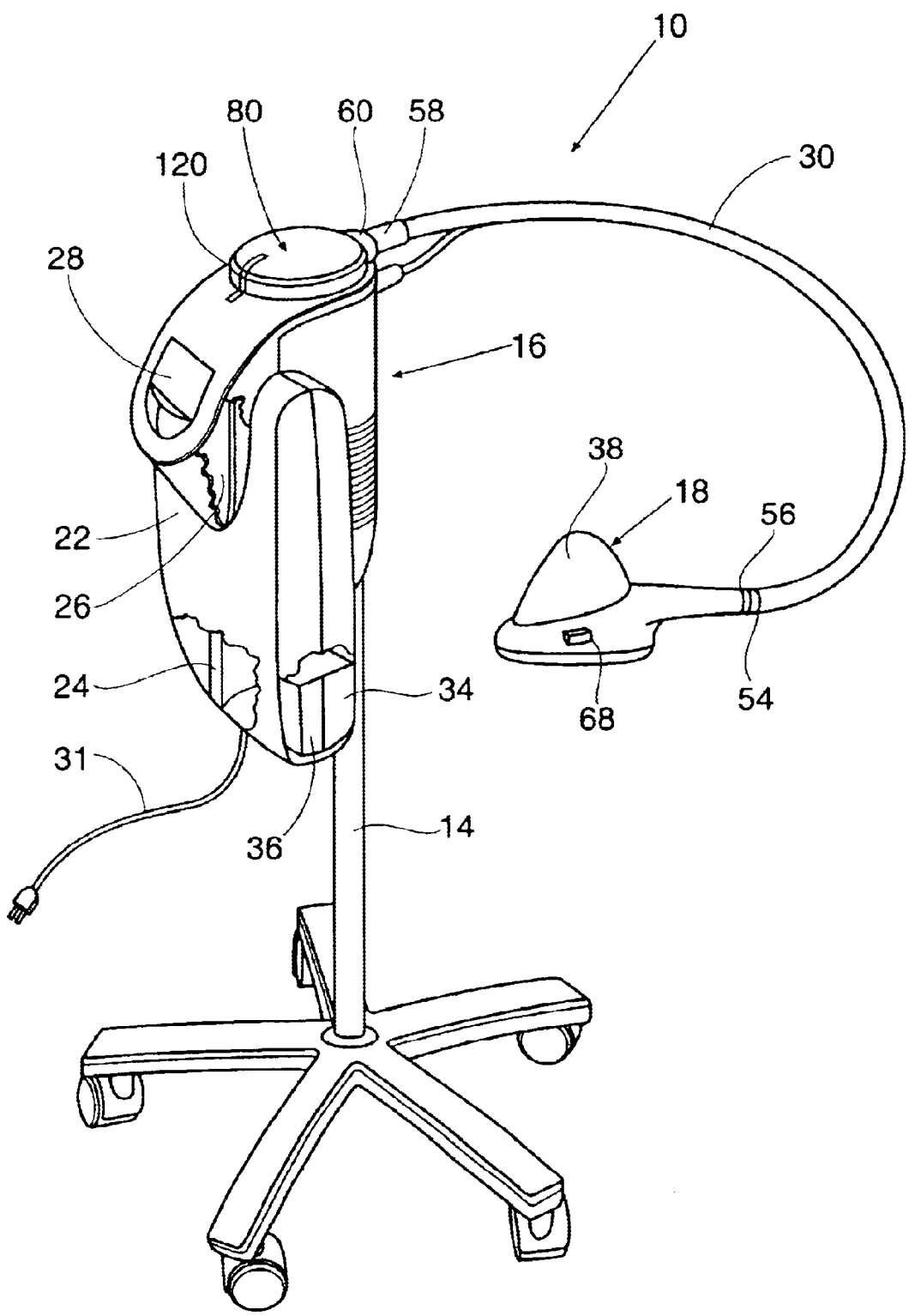
FIG. 1 is a perspective view of a system for transcutaneously applying ultrasonic energy to affect increased blood perfusion.

FIG. 1 schematically shows a compact, portable therapeutic system 10 that makes it possible to treat a person who needs or who is likely to need an increase in the flow rate or perfusion of circulating blood.

The system 10 includes durable and disposable equipment and materials necessary to treat the person at a designated treatment location. In use, the system 10 affects increased blood perfusion by transcutaneously applying ultrasonic energy.

Figure 5:
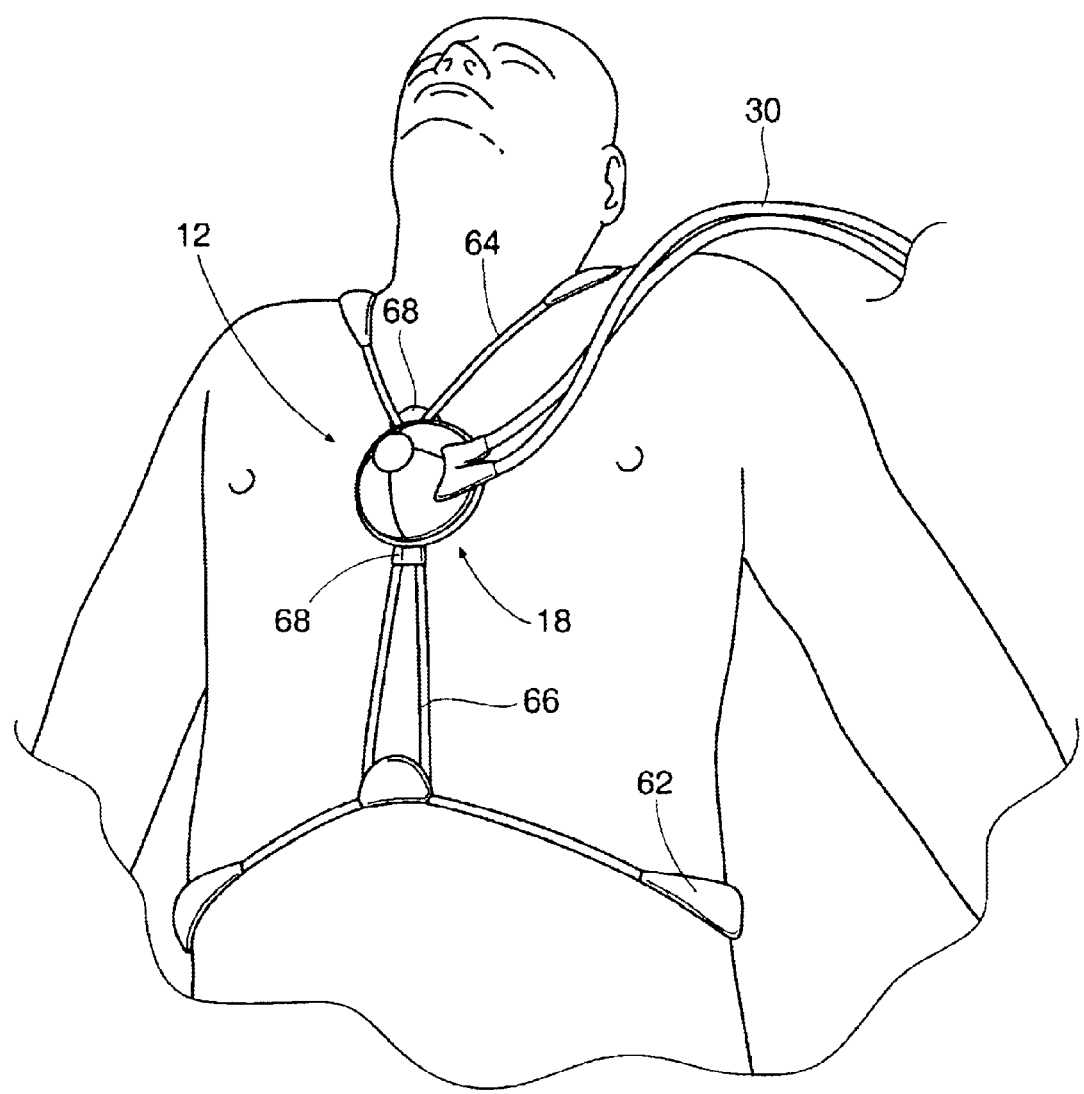
FIG. 5 is a view of the applicator shown in FIG. 2 held by a stabilization assembly in a secure position overlaying the sternum of a patient, to transcutaneously direct ultrasonic energy toward the vasculature of the heart.
Figure 6:
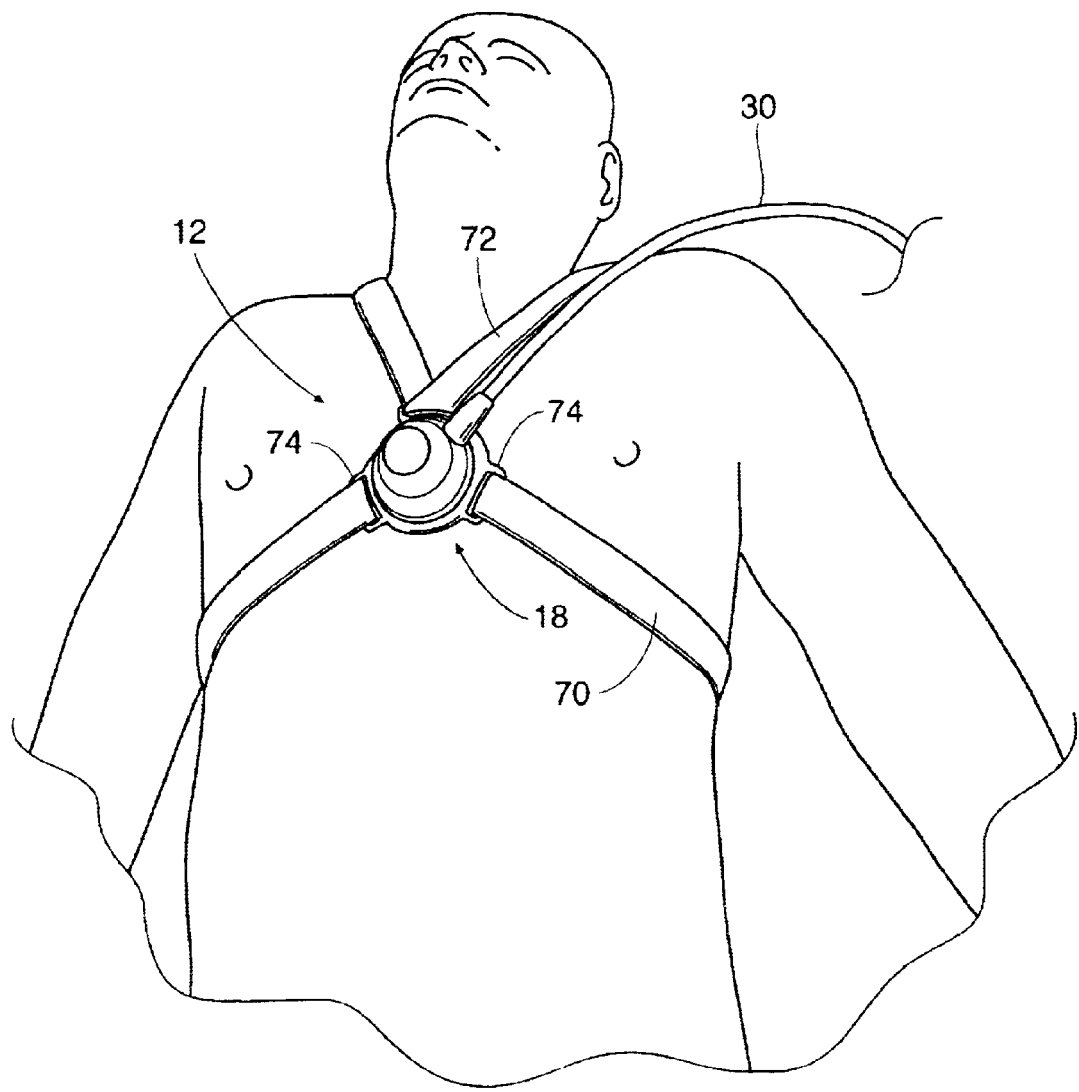
FIG. 6 is a view of the applicator shown in FIG. 2 held by another type of stabilization assembly on the thorax of a patient to transcutaneously direct ultrasonic energy toward the vasculature of the heart.

As FIG. 1 shows, the system 10 includes at the treatment location an ultrasound generating machine 16. The system 10 also includes at the treatment location at least one ultrasound applicator 18, which is coupled to the machine 16 during use. As FIGS. 5 and 6 show, the system 10 also includes an assembly 12 for use with the applicator 18 to stabilize the position of the applicator 18 on a patient for hands-free use. In the illustrated embodiment (see FIGS. 5 and 6), the applicator 18 is secured against movement on a person's thorax, overlaying the sternum, to direct ultrasonic energy toward the vasculature of the heart.

The location where treatment occurs can vary. It can be a traditional clinical setting, where support and assistance by one or more medically trained care givers are immediately available to the person, such as inside a hospital, e.g., in an emergency room, catheter lab, operating room, or critical care unit. However, due to the purposeful design of the system 10, the location need not be confined to a traditional clinical setting. The location can comprise a mobile setting, such as an ambulance, helicopter, airplane, or like vehicle used to convey the person to a hospital or another clinical treatment center. The location can even comprise an everyday, public setting, such as on a cruise ship, or at a sports stadium or airport, or a private setting, such as in a person's home, where the effects of low blood perfusion can arise.

By purposeful design of durable and disposable equipment, the system 10 can make it possible to initiate treatment of a reduced blood perfusion incident in a non-clinical, even mobile location, outside a traditional medical setting. The system thereby makes effective use of the critical time period before the person enters a hospital or another traditional medical treatment center.

The features and operation of the system 10 will now be described in greater detail.

A. The Ultrasound Generator

FIG. 1 shows a representative embodiment of a machine 16. The machine 16 can also be called an "ultrasound generator." The machine 16 is intended to be a durable item capable of long term, maintenance free use.

As shown in FIG. 1, the machine 16 can be variously sized and shaped to present a lightweight and portable unit, presenting a compact footprint suited for transport, e.g., mounted on a conventional pole stand 14, as FIG. 1 shows. This allows the machine 16 to accompany the patient from one location to another. The machine 16 can alternatively be sized and shaped to be mounted at bedside, or to be placed on a table top or otherwise occupy a relatively small surface area. This allows the machine 16 to travel with the patient within an ambulance, airplane, helicopter, or other transport vehicle where space is at a premium. This also makes possible the placement of the machine 16 in a non-obtrusive way within a private home setting, such as for the treatment of chronic angina.

In the illustrated embodiment, the machine 16 includes a chassis 22, which can be made of molded plastic or metal or both. The chassis houses a module 24 for generating electric signals. The signals are conveyed to the applicator 18 by an interconnect 30 to be transformed into ultrasonic energy. A controller 26, also housed within the chassis 22 (but which could be external of the chassis 22, if desired), is coupled to the module 24 to govern the operation of the module 24. Further details regarding the controller 26 will be described later.

The machine 16 also preferably includes an operator interface 28. Using the interface 28, the operator inputs information to the controller 26 to affect the operating mode of the module 24. Through the interface 28, the controller 26 also outputs status information for viewing by the operator. The interface 28 can provide a visual readout, printer output, or an electronic copy of selected information regarding the treatment. The interface 28 is shown as being carried on the chassis 22, but it could be located external of the chassis 22 as well. Further details regarding the interface 28 will be described later.

The machine 16 includes a power cord 31 for coupling to a conventional electrical outlet, to provide operating power to the machine 16. The machine 16 also preferably includes a battery module 34 housed within the chassis 22, which enables use of the machine 16 in the absence or interruption of electrical service. The battery module 34 can comprise rechargeable batteries, that can be built in the chassis 22 or, alternatively, be removed from the chassis 22 for recharge. Likewise, the battery module 34 can include a built-in or removable battery recharger 36. Alternatively, the battery module 34 can comprise disposable batteries, which can be removed for replacement.

Power for the machine 16 can also be supplied by an external battery and/or line power module outside the chassis 22. The battery and/or line power module is releasably coupled at time of use to the components within the chassis 22, e.g., via a power distribution module within the chassis 22.

The provision of battery power for the machine 16 frees the machine 16 from the confines surrounding use of conventional ultrasound equipment, caused by their dependency upon electrical service. This feature makes it possible for the machine 16 to provide a treatment modality that continuously "follows the patient," as the patient is being transported inside a patient transport vehicle, or as the patient is being shuttled between different locations within a treatment facility, e.g., from the emergency room to a holding area within or outside the emergency room.

In a representative embodiment, the chassis 22 measures about 12 inches×about 8 inches×about 8 inches and weighs about 9 pounds.

B. The Ultrasound Applicator

Figure 2:
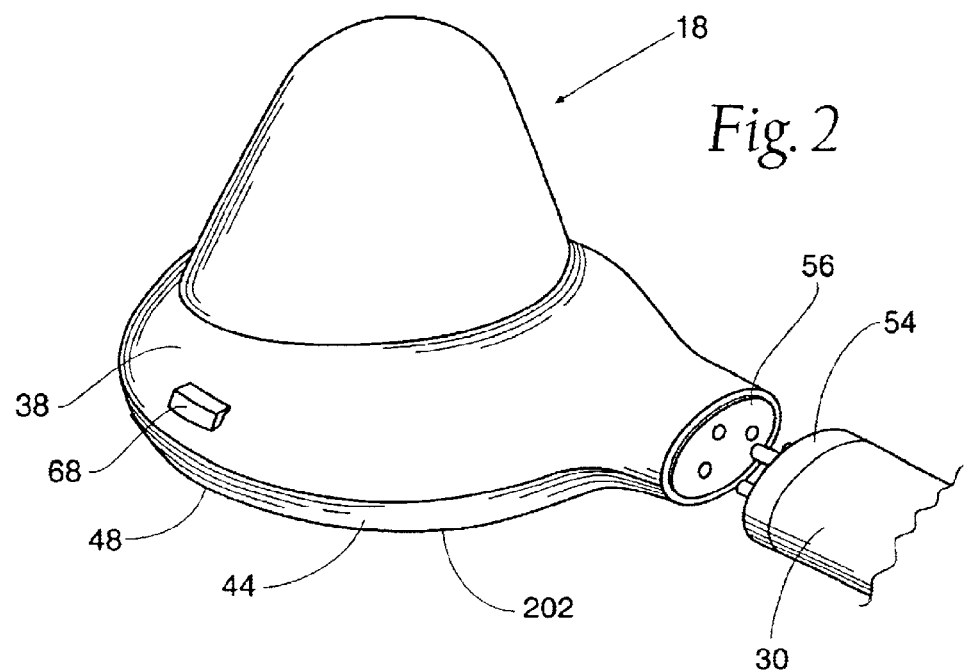
FIG. 2 is an enlarged side perspective view of an ultrasonic applicator that forms a part of the system shown in FIG. 1.
Figure 3:
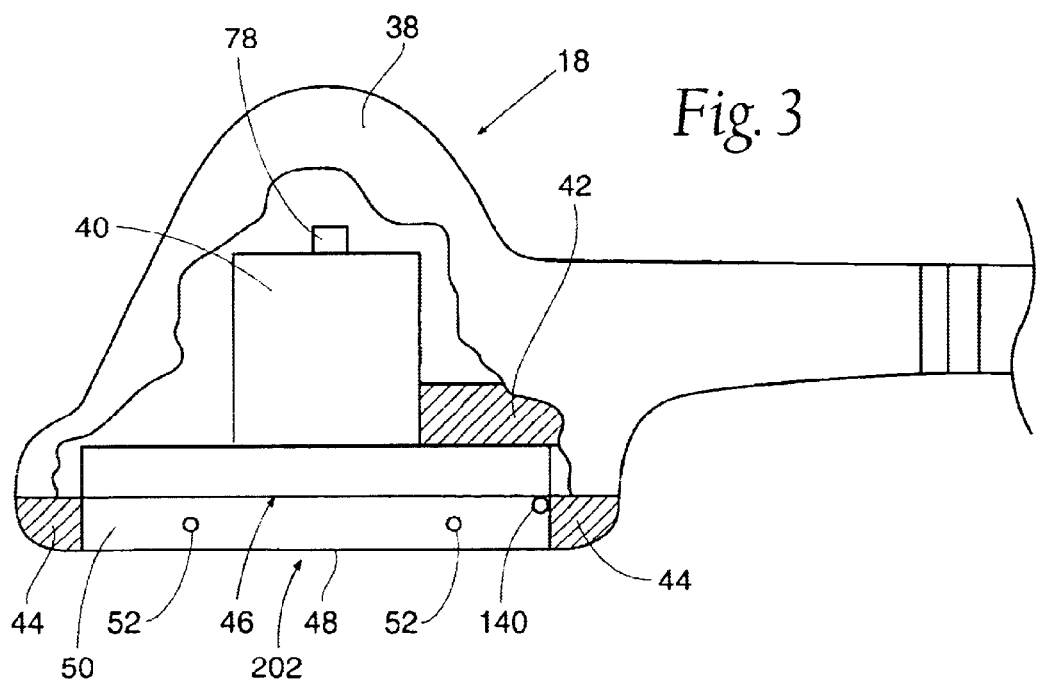
FIG. 3 is a side section view, with parts broken away and in section of the applicator shown in FIG. 2.

As best shown in FIGS. 2 and 3, the applicator 18 can also be called the "patient interface." The applicator 18 comprises the link between the machine 16 and the treatment site within the thoracic cavity of the person undergoing treatment. The applicator 18 converts electrical signals from the machine 16 to ultrasonic energy, and further directs the ultrasonic energy to the targeted treatment site.

Desirably, the applicator 18 is intended to be a disposable item. At least one applicator 18 is coupled to the machine 16 via the interconnect 30 at the beginning a treatment session. The applicator 18 is preferably decoupled from the interconnect 30 (as FIG. 2 shows) and discarded upon the completing the treatment session. However, if desired, the applicator 18 can be designed to accommodate more than a single use.

As FIGS. 2 and 3 show, the ultrasound applicator 18 includes a shaped metal or plastic body 38 ergonomically sized to be comfortably grasped and manipulated in one hand. The body 38 houses at least one ultrasound transducer 40 (see FIG. 3).

The body 38 can include a heat sink region 42 placed about the transducer 40, to conduct heat generated by the transducer or transducers during operation, to minimize heating effects. As will be described later, impedance matching or active cooling can also be achieved to prevent or counter heating effects.

Preferably, the plastic body 38 includes a stand-off region 44 or skirt extending from the front mass or face 46 of the transducer 40. The skirt region 44 enables spacing the transducer face 46 a set distance from the patient's skin. The skirt region 44 prevents direct contact between the transducer face 46 and the person's skin. In a preferred arrangement, the skirt region 44 is formed of a soft material, such as foam.

In a preferred embodiment, the front mass 46 of the transducer 40 measures about 2 inches in diameter, whereas the acoustic contact area 202 formed by the skirt region 44 measures about 4 inches in diameter. An applicator 18 that presents an acoustic contact area 202 of significantly larger diameter than the front mass of the transducer 40 (e.g., in a ratio of at least 2:1) reduces overall weight and makes possible an ergonomic geometry (like that shown in FIG. 2) that enables single-handed manipulation during setup, even in confined quarters, and further provides (with the assembly 12) hands-free stability during use. In a representative embodiment, the applicator 18 measures about 4 inches in diameter about the skirt region 44, about 4 inches in height, and weighs about one pound.

The material 48 defines a bladder chamber 50 between it and the transducer face 46. The bladder chamber 50 accommodates a volume of an acoustic coupling media liquid, e.g., liquid, gel, oil, or polymer, that is conductive to ultrasonic energy, to further cushion the contact between the applicator 18 and the skin. The presence of the acoustic coupling media also makes the acoustic contact area 202 of the material 48 more conforming to the local skin topography.

Figure 4:
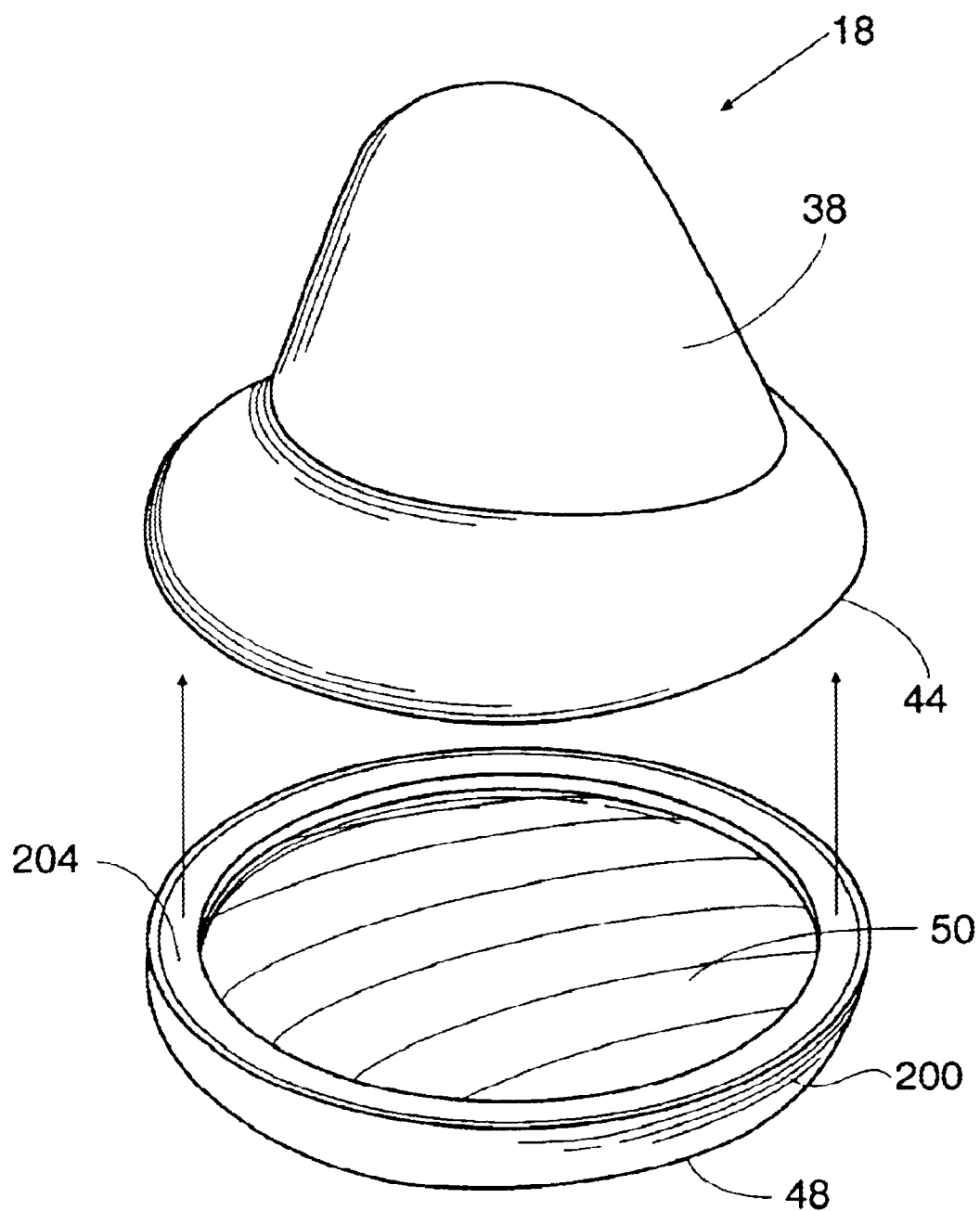
FIG. 4 is an enlarged side perspective view of an alternative embodiment of an ultrasonic applicator having an ultrasonic conductive pad that can be joined to the applicator for use as part of the system shown in FIG. 1.

The material 48 and bladder chamber 50 can together form an integrated part of the applicator 18. Alternatively, as shown in FIG. 4, the material 48 and bladder chamber 50 can be formed by a separate molded component, e.g., a gel or liquid filled pad 200, which is not an integral part of the applicator 18, but which is supplied separately. In this arrangement, the separate component 200 can be releasably attached, e.g., by an adhesive strip 204 or the like on the pad 200, to the transducer face 46 or to the skirt 44, if present, at instant of use. A molded gel filled pad adaptable to this purpose is the AQUAFLEX® Ultrasound Gel Pad sold by Parker Laboratories (Fairfield, N.J.).

As will be described later, an acoustic coupling media may be circulated through ports 52 (see FIG. 3) into and out of the bladder chamber 50, to conduct heat from the bladder chamber 50 and/or perform a function to maintain a desired impedance value.

The interconnect 30 carries a distal connector 54 (see FIG. 2), designed to easily plug into a mating outlet 56 in the transducer 40. A proximal connector 58 on the interconnect 30 likewise easily plugs into a mating outlet 60 on the chassis 22 (see FIG. 1), which is itself coupled to the controller 26. In this way, the applicator 18 can be quickly connected to the machine 16 at time of use, and likewise quickly disconnected for discard once the treatment session is over. Other quick-connect coupling mechanisms can be used. It should also be appreciated that the interconnect 30 can be hard wired as an integrated component to the applicator 18 with a proximal quick-connector 58 to plug into the chassis 22, or, vice versa, the interconnect 30 can be hard wired as an integrated component to the chassis 22 with a distal quick-connector 54 to plug into the applicator 18.

As FIG. 5 shows, a stabilization assembly 12 allows the operator to temporarily but securely mount the applicator 18 against an exterior skin surface for use. In the illustrated embodiment, since the treatment site exists in the thoracic cavity, the attachment assembly 54 is fashioned to secure the applicator 18 on the person's thorax, overlaying the sternum or breastbone, as FIG. 5 shows.

Just as the applicator 18 can be quickly coupled to the machine 16 at time of use, the stabilization assembly 12 also preferably makes the task of securing and removing the applicator 18 on the patient simple and intuitive. Thus, the stabilization assembly 12 makes it possible to secure the applicator 18 quickly and accurately in position on the patient in cramped quarters or while the person (and the system 10 itself) is in transit.

The stabilization assembly 12 can be variously constructed. In the embodiment shown in FIG. 5, the stabilization assembly 12 comprises a sling 62 worn on the back of the patient between the waist and shoulders. The sling 62 carries a shoulder loop 64 and a waist loop 66. The loops 64 and 66 are made of a stretchable, elastic material. The loops 64 and 66 can be stretched to hook into flanges 68 formed on the body 38 of the applicator 18 (also shown in FIG. 2). The stretchable loops 64 and 66 allow for a rapid mounting and removal of the applicator 18 on the thorax of the patient. The stretchable loops 64 and 66 also securely hold the applicator 18 in a stable position on the patient, even in the midst of a dynamic and mobile environment.

As FIG. 5 shows, the stabilization assembly 12 preferably occupies only a relatively small area on the chest. The stabilization assembly 12 (and the compact size of the applicator 18 itself) allow other devices, e.g., a twelve lead ECG electrode device, to be placed on the chest at the same time the applicator 18 is being used.

In another embodiment (see FIG. 6), the stabilization assembly 12 comprises halter straps 70 and 72 worn about the chest and shoulders of the patient. The straps 70 and 72 are made of quick release material, e.g., from Velcro™ material. The straps can be easily passed through rings 74 formed in the body 38 of the applicator 18, and doubled back upon themselves to be secured together. This arrangement, like the arrangement shown in FIG. 5, allows for rapid placement and removal of the applicator 18 on the thorax (sternum) of the patient. Also, like the stabilization assembly 12 shown in FIG. 5, the assembly 12 shown in FIG. 6 also does not to impede the placement of other treatment devices on the thorax simultaneously with the applicator 18.

For added comfort in either embodiment of the stabilization assembly 12, the sling 62 or halter strips 70/72 can be attached to a flexible back piece (not shown) worn on the patient's back. The back piece can comprise, e.g., a flexible cloth or plastic sheet or pad, formed in the manner of the back half of a vest. The slings 62 or halter straps 70/72 are sown or buckled to the back piece and extend forward about the shoulders and chest of the patient, to be coupled to the applicator 18 in the fashion shown FIGS. 5 and 6 show. The sling 62 or halter straps 70/72 transfer the weight of the applicator 18 to the back piece. The back piece distributes the weight borne by the sling 62 or halter straps 70/72 in a uniform manner across the patient's back.

Figure 7:
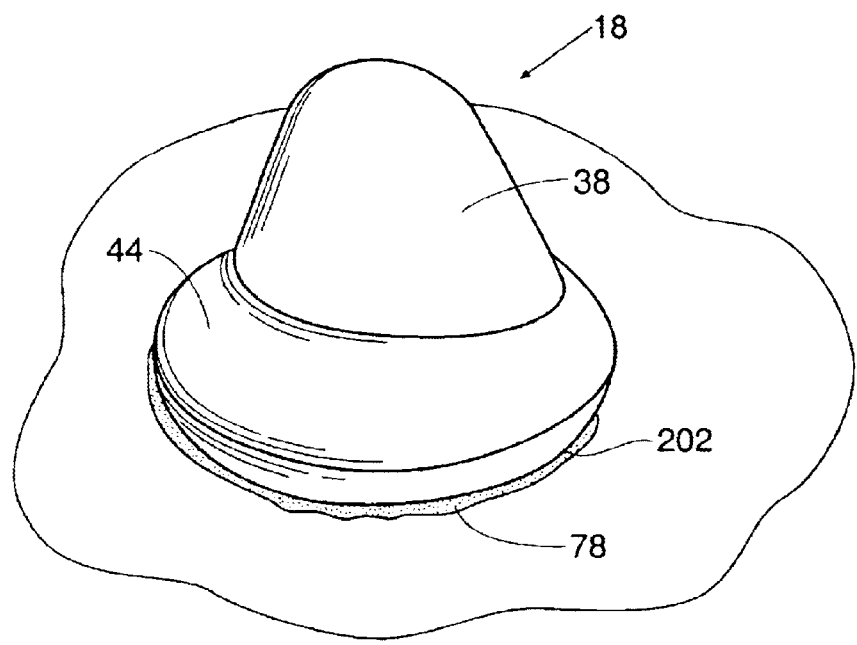
FIG. 7 is an enlarged side perspective view of an ultrasonic applicator of the type shown in FIG. 2 used in association with an ultrasonic material externally applied to the skin.

If desired (see FIG. 7), an external ultrasound conducting material 78 can also be applied directly to the skin of the person, to provide acoustic coupling between the applicator 18 and the treatment site. The external material 78 can comprise, e.g., a gel material (such as AQUASONIC® 100, by Parker Laboratories, Inc., Fairfield, N.J.). The external material 78 can possess sticky or tacky properties, to further enhance the securement of the applicator 18 to the skin.

Figure 8:
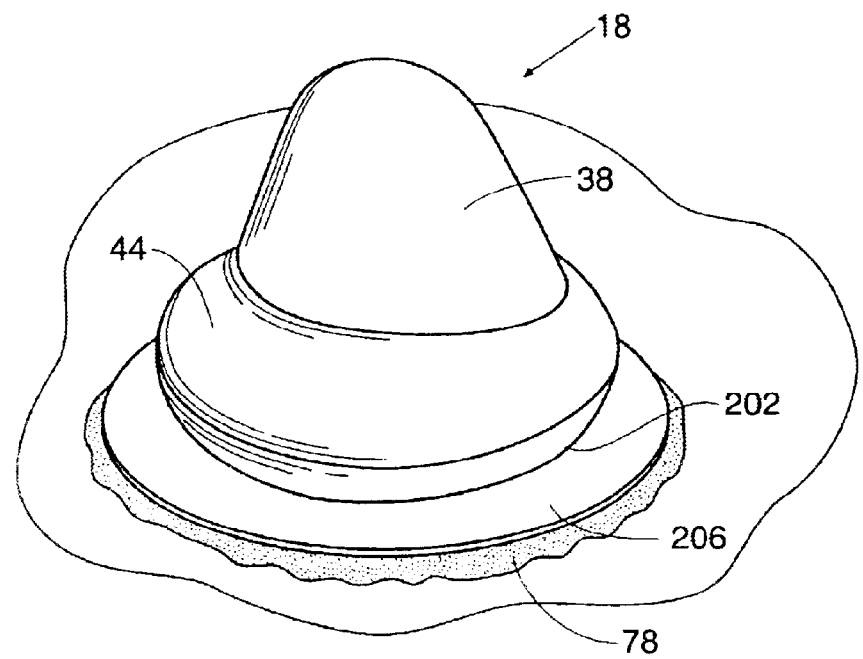
FIG. 8 is an enlarged side perspective view of an ultrasonic applicator of the type shown in FIG. 2 used in association with a patch externally applied to the skin to create a clean ultrasonic interface.

Alternatively or in combination with a gel material 78 (see FIG. 8), an adherent patch 206 can be secured on the individual skin. The patch 206 forms a clean interface surface between the acoustic contact area 202 of the applicator 18 and the individual's skin. The patch 206 keeps the interface surface free from body hair, perspiration, and other materials that can interfere with the direct transcutaneous transmission of ultrasonic energy.

Figure 9:
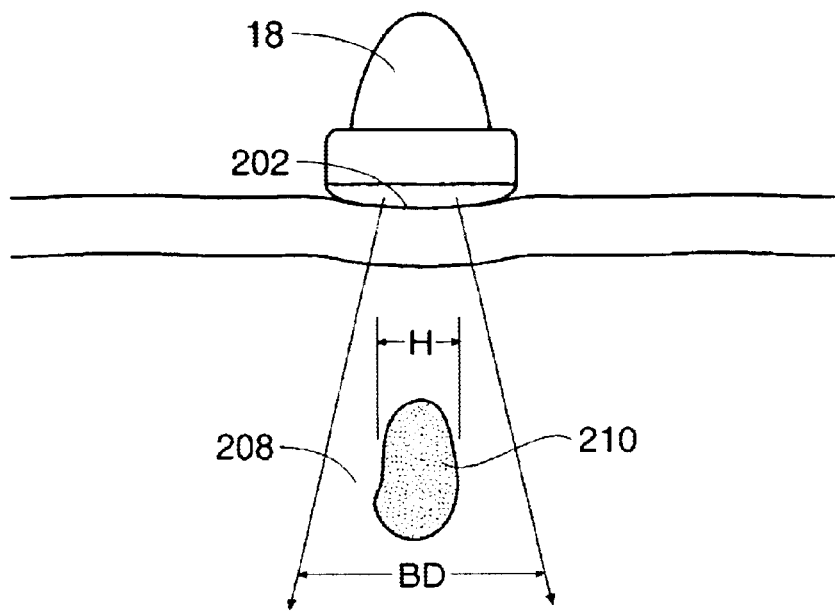
FIG. 9 is a schematic view of an ultrasonic applicator of the type shown in FIG. 2 positioned to transcutaneously apply ultrasonic energy to the heart in the thoracic cavity, showing a desired degree of ultrasonic energy beam divergence that applies ultrasonic energy substantially to the whole heart.

The applicator 18 can be formed in various shapes for ease of storage, handling, and use. As FIGS. 2 and 3 show, the applicator 18 can comprise generally discus or hockey puck shape. As FIG. 9 shows, the applicator 18 can be shaped in a more elliptical or elongated fashion that aligns with the axis of the sternum or heart, for example. In this arrangement, passage of ultrasonic energy into adjacent organs, e.g., the lungs, is minimized.

C. Aperture (Directivity)

Desirably, when used to apply ultrasonic energy transcutaneously in the thoracic cavity to the heart, the transducer face 46 is sized to deliver ultrasonic energy in a desired range of fundamental frequencies to substantially the entire targeted region. Generally speaking, the fundamental frequencies of ultrasonic energy suited for transcutaneous delivery to the heart in the thoracic cavity to increase blood perfusion can lay in the range of about 500 kHz or less. Desirably, the fundamental frequencies for this indication lay in a frequency range of about 20 kHz to about 100 kHz, e.g., about 27 kHz.

Within this range of fundamental frequencies (see FIG. 9), the transducer face 46 of the applicator 18 should be sized to percutaneously transmit the energy in a diverging beam 208 which substantially covers the entire heart and coronary circulation 218. The applicator 18 may comprise a single transducer (as FIG. 9 shows) or an array of transducers that together form an acoustic contact area 202.

Normal hearts vary significantly in size and distance from skin between men and women, as well as among individuals regardless of sex. Typically, for men, the size of a normal heart ranges between 8 to 11 cm in diameter and 6 to 9 cm in depth, and the weight ranges between 300 to 350 grams. For men, the distance between the skin and the anterior surface of the heart (which will be called the "subcutaneous depth" of the heart) ranges between 4 to 9 cm. Typically, for women, the size of a normal heart ranges between 7 to 9 cm in diameter and 5 to 8 cm in depth, and the weight ranges between 250 to 300 grams. For women, the subcutaneous depth of the heart ranges between 3 to 7 cm.

The degree of divergence or "directivity" of the ultrasonic beam 208 transmitted percutaneously through the acoustic contact area 202 is a function of the wavelength of the energy being transmitted. Generally speaking, as the wavelength increases, the beam divergence (shown generally as BD in FIG. 9) becomes larger (given a fixed aperture size). If the beam divergence BD at the subcutaneous depth of the heart 210 is less than beam area of the heart 210 (shown as H in FIG. 9), the ultrasonic energy will not be delivered to substantially the whole heart. Therefore, the beam divergence BD should desirably be essentially equal to or greater than the targeted beam area H at the subcutaneous depth of the heart 210.

Within the desired range of fundamental frequencies of 20 kHz to 100 kHz, the beam divergence can be expressed in terms of an aperture size measured in wavelengths. The aperture size (AP) can be expressed as a ratio between the effective diameter of the transducer face 46 (D) and the wavelength of the ultrasonic energy being applied (WL), or AP=D/WL. For example, a transducer face 46 having an effective diameter (D) of 4 cm, transmitting at a fundamental frequency of about 48 kHz (wavelength (WL) of 3 cm), can be characterized as having an aperture size of ⁴⁄₃ wavelengths, or 1.3 wavelengths. The term "effective diameter" is intended to encompass a geometry that is "round," as well as a geometry that is not "round", e.g., being elliptical or rectilinear, but which possesses a surface area in contact with skin that can be equated to an equivalent round geometry of a given effective diameter.

For the desired range of fundamental frequencies of 20 kHz to about 100 kHz, transducer faces 46 characterized by aperture sizes laying within a range of 0.5 to 5 wavelengths, and preferably less than 2 wavelengths, possess the requisite degree of beam divergence to transcutaneously deliver ultrasonic energy from a position on the thorax, and preferably on or near the sternum, to substantially an entire normal heart of a man or a woman.

Of course, using the same criteria, the transducer face 46 can be suitably sized for other applications within the thoracic cavity or elsewhere in the body. For example, the transducer face 46 can be sized to delivery energy to beyond the heart and the coronary circulation, to affect the pulmonary circulation.

D. Reduced Localized Cavitational-Cause Heating

In addition to desirably possessing the characteristic of coupling energy to substantially the entire targeted tissue region, the acoustic contact area 202 desirably is configured to minimize localized skin surface heating effects.

Figure 10:
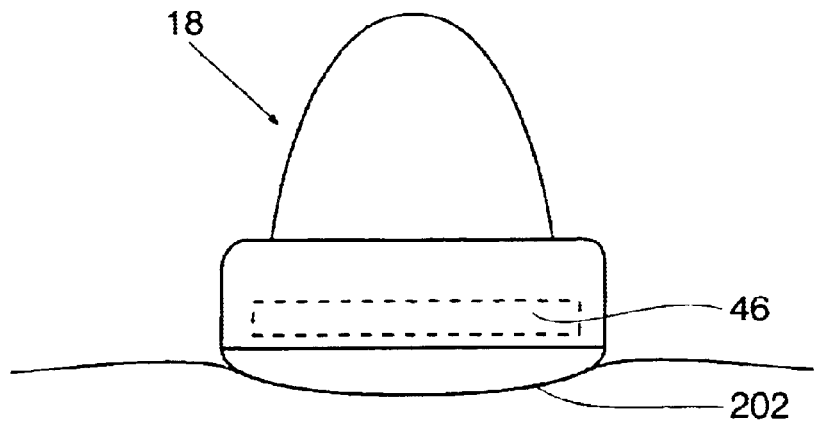
FIG. 10 is a side elevation view of an ultrasonic applicator having a flexible ultrasound radiating surface that can conform evenly to a skin surface region, eliminating gaps between the radiating surface and the skin, to thereby mediate localized conductive heating effects during use.
Figure 11:
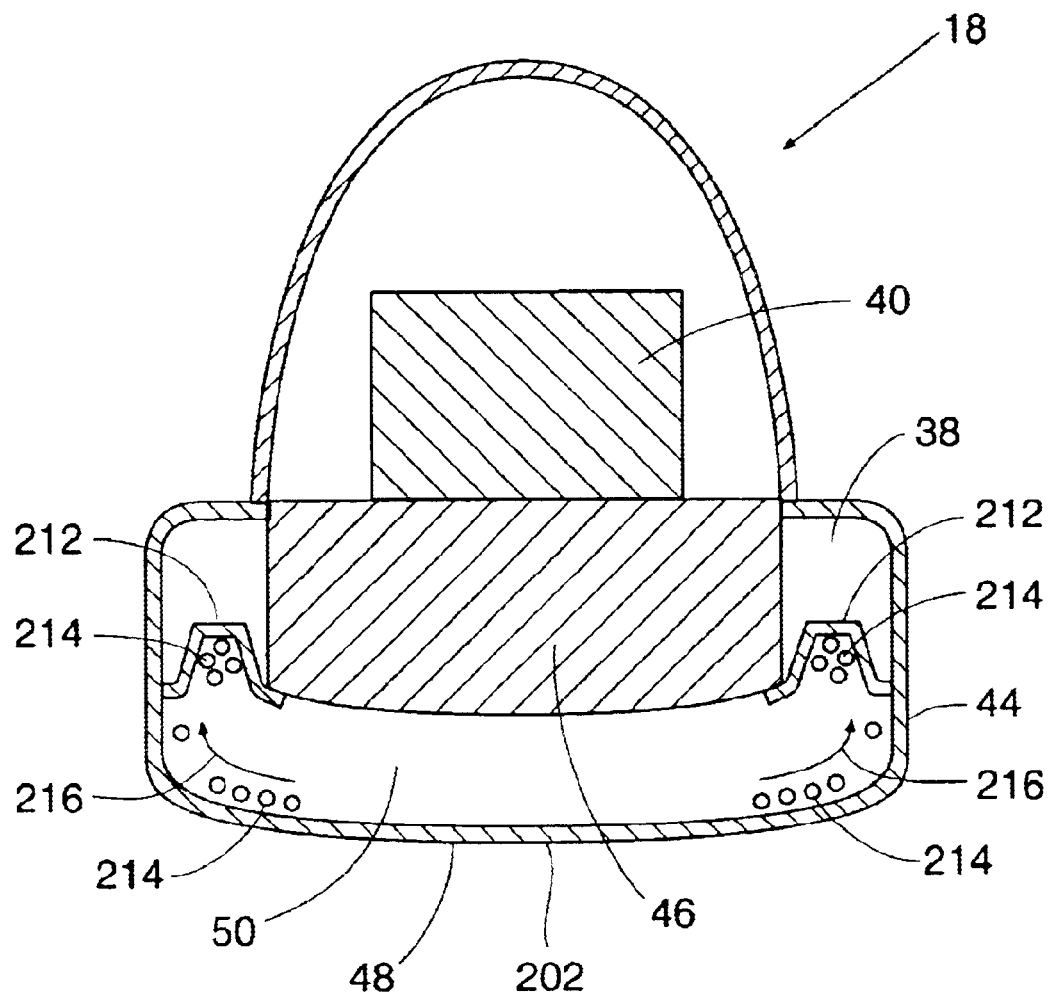
FIG. 11 is a side section view of an ultrasonic application of the type shown in FIG. 10, and also showing and interior well region surrounding the transducer face for collecting air to further mediate localized conductive heating effects during use.

Localized skin surface heating effects may arise by the presence of air bubbles trapped between the acoustic contact area 202 and the individual's skin. In the presence of ultrasonic energy, the air bubbles vibrate, and thereby may cause cavitation and attendant conductive heating effects at the skin surface. To minimize the collection of air bubbles along the acoustic contact area 202, the acoustic contact area 202 desirably presents a flexible, essentially flat radiating surface contour where it contacts the individual's skin (as FIG. 3 shows), or a flexible, outwardly bowed or convex radiating surface contour (i.e., curved away from the transducer face 46) where it contacts with or conducts acoustic energy to the individual's skin (as FIGS. 10 and 11 show). Either a flexible flat or convex surface contour can "mold" evenly to the individual's skin topography, to thereby mediate against the collection and concentration of air bubbles in the contact area 202 where skin contact occurs. In comparison, an inwardly bowed or concave contact area 202 (i.e., curved toward the transducer face 46) is more prone to air bubble collection in the region of skin contact, and thereby may be more subject to cavitation-caused localized skin surface heating.

To further mediate against cavitation-caused localized skin surface heating (see FIG. 11), the interior of the bladder chamber 50 can include a recessed well region 212 surrounding the transducer face 46. The well region 212 is located at a higher gravity position than the plane of the transducer face 46. Air bubbles 214 that may form in fluid located in the bladder chamber 50 are led by gravity to collect in the well region 212 away from the ultrasonic energy beam path. A convex contact area 202 (as shown in FIG. 11) further enhances the gravity-assisted collection of air bubbles 214 in the well region 212, as shown by arrows 216 in FIG. 11. The air bubbles 214, to the extent they form, are kept away from the region of skin contact and out of the path of the ultrasonic energy beam. To minimize the possibility of air bubbles being present in the ultrasonic beam, the transducer face 46 may also be convex in shape (as FIG. 11 shows).

II. Use of the System with a Therapeutic Agent

Figure 12:
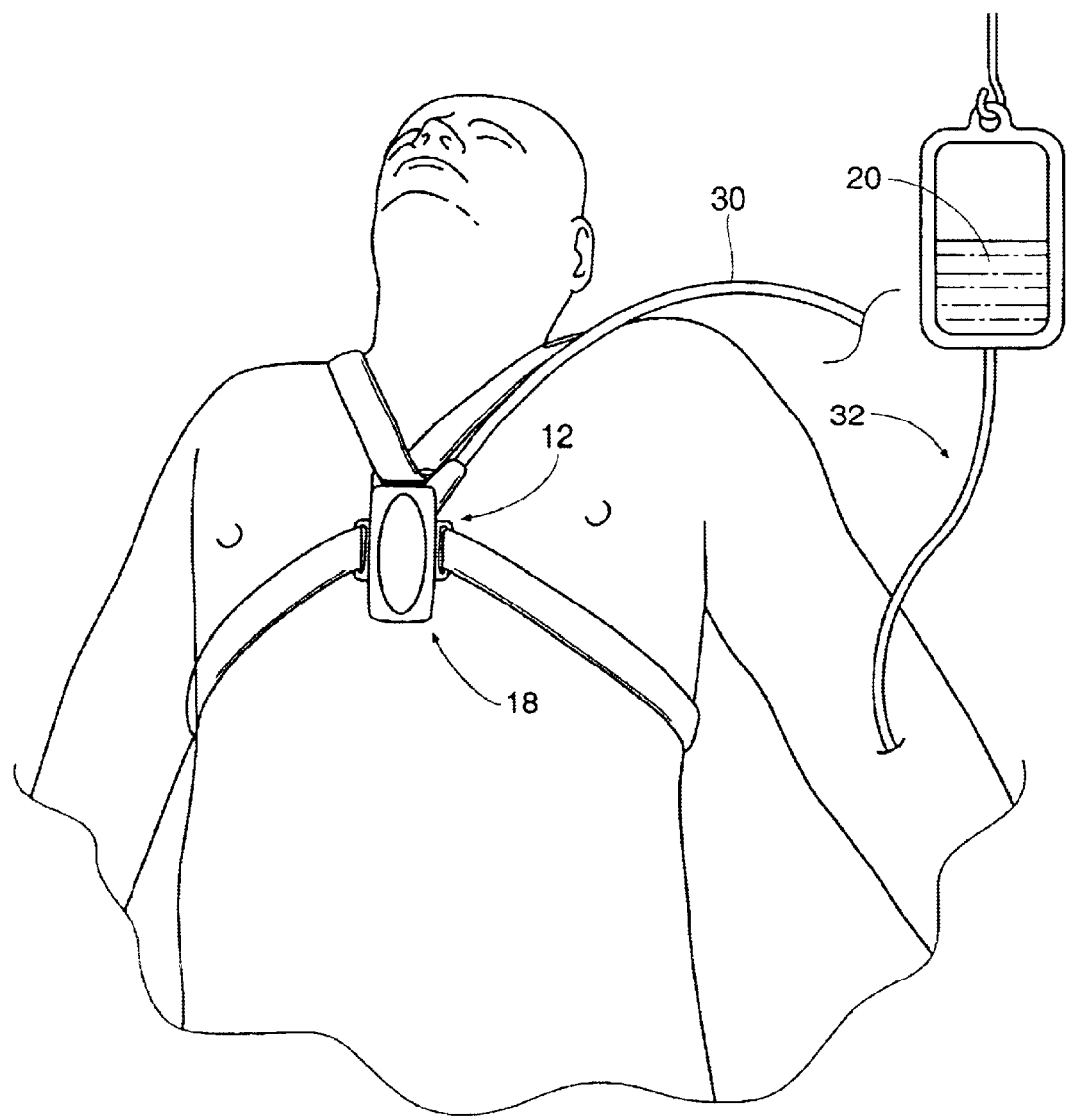
FIG. 12 is a view of another embodiment of an ultrasonic applicator usable in association with the system shown in FIG. 1, the applicator being shaped to apply ultrasonic energy to the vasculature in the heart without passage through adjacent organs like the lungs, the system also including an assembly to administer a therapeutic agent in conjunction with the application of ultrasonic energy.

As FIG. 12 shows, the system 10 can further include at the treatment location a delivery system 32 for introducing a therapeutic agent 20 in conjunction with the use of the applicator 18 and machine 16. In this arrangement, the effect of increased blood perfusion caused by the application of ultrasonic energy can also be enhanced by the therapeutic effect of the agent 20, or vice versa. Application of ultrasound within the range of fundamental frequencies of about 20 kHz to about 100 kHz at a power density equal to or less than about 3 W/cm$^2$ and at a maximum total power output between 15 W and 150 W increases coronary vessel diameter approximately 10%, which results in a 46% increase in blood flow.

A. Use with a Thrombolytic Agent

For example, the therapeutic agent 20 can comprise a thrombolytic agent. In this instance, the thrombolytic agent 20 is introduced into a thrombosis site (using the delivery system 32), prior to, in conjunction with, or after the application of ultrasound. The interaction between the applied ultrasound and the thrombolytic agent 20 is observed to assist in the break-down or dissolution of the thrombi, compared with the use of the thrombolytic agent 20 in the absence of ultrasound. This phenomenon is discussed, e.g., in Carter U.S. Pat. No. 5,509,896; Siegel et al U.S. Pat. No. 5,695,460; and Lauer et al U.S. Pat. No. 5,399,158, which are each incorporated herein by reference.

The process by which thrombolysis is affected by use of ultrasound in conjunction with a thrombolytic agent 20 can vary according to the frequency, power, and type of ultrasonic energy applied, as well as the type and dosage of the thrombolytic agent 20. The application of ultrasound has been shown to cause reversible changes to the fibrin structure within the thrombus, increased fluid dispersion into the thrombus, and facilitated enzyme kinetics. These mechanical effects beneficially enhance the rate of dissolution of thrombi. In addition, cavitational disruption and heating/streaming effects can also assist in the breakdown and dissolution of thrombi.

The type of thrombolytic agent 20 used can vary. The thrombolytic agent 20 can comprise a drug known to have a thrombolytic effect, such as t-PA, TNKase, or RETAVASE. Alternatively (or in combination), the thrombolytic agent 20 can comprise an anticoagulant, such as heparin; or an antiplatelet drug, such as a GP IIb IIIa; or a fibrinolytic drug; or a non-prescription agent having a known beneficial effect, such as aspirin. Alternatively (or in combination) the thrombolytic agent 20 can comprise microbubbles, which can be ultrasonically activated; or microparticles, which can contain albumin.

The thrombolytic syndrome being treated can also vary, according to the region of the body. For example, in the thoracic cavity, the thrombolytic syndrome can comprise acute myocardial infarction, or acute coronary syndrome. The thrombolytic syndrome can alternatively comprise suspect myocardial ischemia, prinzmetal angina, chronic angina, or pulmonary embolism.

The thrombolytic agent 20 is typically administered by the delivery system 32 intravenously prior to or during the application of ultrasonic energy. The dosage of the thrombolytic agent 20 is determined by the physician according to established treatment protocols.

It may be possible to reduce the typical dose of thrombolytic agent 20 when ultrasonic energy is also applied. It also may be possible to use a less expensive thrombolytic agent 20 or a less potent thrombolytic agent 20 when ultrasonic energy is applied. The ability to reduce the dosage of thrombolytic agent 20, or to otherwise reduce the expense of thrombolytic agent, or to reduce the potency of thrombolytic agent, when ultrasound is also applied, can lead to additional benefits, such as decreased complication rate, an increased patient population eligible for the treatment, and increased locations where the treatment can be administered (i.e., outside hospitals and critical care settings, such as in ambulances, helicopters, other public settings, as well as in private, in-home settings).

B. Use with an Angiogenic Agent

Treatment using ultrasound alone can stimulate additional capillary or microcirculatory activity, resulting in an angiogenesis effect. This treatment can be used as an adjunct to treatment using angiogenic agents released in the coronary circulation to promote new arterial or venous growth in ischemic cardiac tissue or elsewhere in the body. In this instance, the therapeutic agent 20 shown in FIG. 12 can comprise an angiogenic agent, e.g., Monocyte Chemoattractant Protein-1, or Granulocyte-Macrophage Colony-Stimulating-Factor.

It is believed that the angiogenic effects of these agents can be enhanced by shear-related phenomena associated with increased blood flow through the affected area. Increased blood perfusion in the heart caused by the application of ultrasound energy can induce these shear-related phenomena in the presence of the angiogenic agents, and thereby lead to increased arterial-genesis and/or vascular-genesis in ischemic heart tissue.

III. Use of the System With Other Treatment Applications

The system 10 can be used to carry out other therapeutic treatment objectives, as well.

For example, the system 10 can be used to carry out cardiac rehabilitation. The repeated application of ultrasound over an extended treatment period can exercise and strengthen heart muscle weakened by disease or damage. As another example, treatment using ultrasound can facilitate an improvement in heart wall motion or function.

Figure 13:
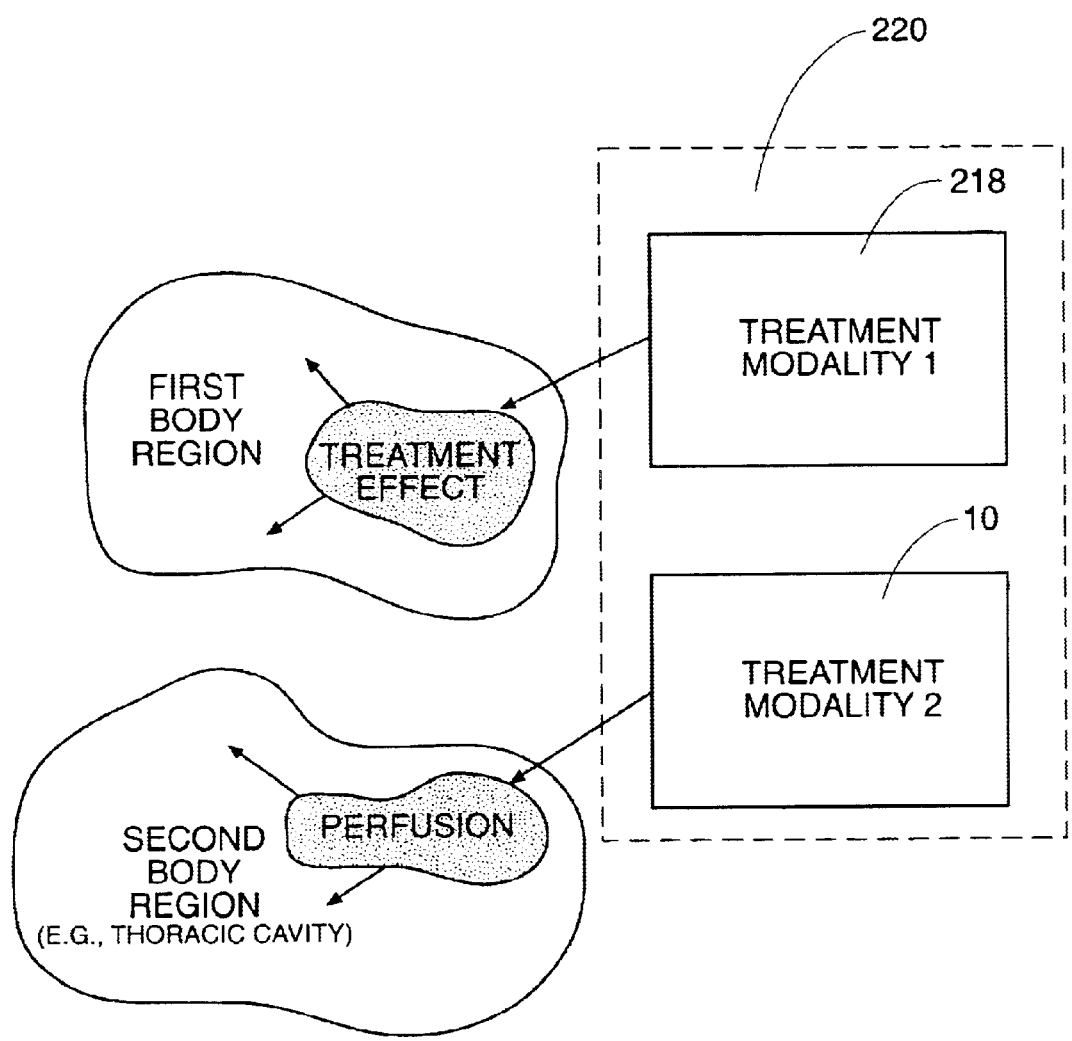
FIG. 13 is a schematic view of a system for achieving different localized systemic treatments in different regions of the body, one of which involves the use of the system shown in FIG. 1.

The system 10 may also be used in associated with other diagnostic or therapeutic modalities to achieve regional systemic therapy. For example, FIG. 13 shows a composite system 220 for achieving regional systemic therapy. The composite system 220 includes a first selected treatment modality 218, which is applied to the body to achieve a desired systemic effect (for example, the restriction of blood flow). The composite system 220 includes a second selected treatment modality, which comprises the ultrasound delivery system 10 previously described. The system 10 is operated before, during, or after the treatment modality 218, at least for a period of time, to transcutaneously apply ultrasonic energy to a selected localized region of the body (e.g., the thoracic cavity) to achieve a different, and perhaps opposite, localized system result, e.g., increased blood perfusion.

For example, an individual who has received a drug that systemically restricts blood flow may experience a need for increased blood perfusion to the heart, e.g., upon experiencing a heart attack. In this situation, the ultrasound delivery system 10 can be used to locally apply ultrasound energy to the thoracic cavity, to thereby locally increase blood perfusion to and in the heart, while systemic blood perfusion remains otherwise lowered outside the thoracic cavity due to the presence of the flow-restricting drug in the circulatory system of the individual.

As another example, a chemotherapy drug may be systemically or locally delivered (by injection or by catheter) to an individual. The ultrasound delivery system 10 can be used to locally supply ultrasound energy to the targeted region, where the tumor is, to locally increase perfusion or uptake of the drug.

The purposeful design of the durable and disposable equipment of the system 10 makes it possible to carry out these therapeutic protocols outside a traditional medical setting, such as in a person's home.

IV. Exemplary Treatment Modalities

As is apparent, the system 10 can accommodate diverse modalities to achieve desired treatment protocols and outcomes. These modalities, once identified, can be preprogrammed for implementation by the controller 26.

A. Controlling Output Frequency

Depending upon the treatment parameters and outcome desired, the controller 26 can operate a given transducer 40 at a fundamental frequency below about 50 kHz, or in a fundamental frequency range between about 50 kHz and about 1 MHz, or at fundamental frequencies above 1 MHz.

A given transducer 40 can be operated in either a pulsed or a continuous mode, or in a hybrid mode where both pulsed and continuous operation occurs in a determined or random sequence at one or more fundamental frequencies.

The applicator 18 can include multiple transducers 40 (or multiple applicators 18 can be employed simultaneously for the same effect), which can be individually conditioned by the controller 26 for operation in either pulsed or continuous mode, or both. For example, the multiple transducers 40 can all be conditioned by the controller 26 for pulsed mode operation, either individually or in overlapping synchrony. Alternatively, the multiple transducers 40 can all be conditioned by the controller 26 for continuous mode operation, either individually or in overlapping synchrony. Still alternatively, the multiple transducers 40 can be conditioned by the controller 26 for both pulsed and continuous mode operation, either individually or in overlapping synchrony.

One or more transducers 40 within an array of transducers 40 can also be operated at different fundamental frequencies. For example, one or more transducers 40 can be operated at about 25 kHz, while another one or more transducers 40 can be operated at about 100 kHz. More than two different fundamental frequencies can be used, e.g., about 25 kHz, about 50 kHz, and about 100 kHz.

Operation at different fundamental frequencies provides different effects. For example, given the same power level, at about 25 kHz, more cavitation effects are observed to dominate, while above 500 kHz, more heating effects are observed to dominate.

The controller 26 can trigger the fundamental frequency output according to time or a physiological event (such as ECG or respiration).

B. Controlling Output Power Parameters

Also depending upon the treatment parameters and outcome desired, the controller 26 can operate a given transducer 40 at a prescribed power level, which can remain fixed or can be varied during the treatment session. The controller 26 can also operate one or more transducers 40 within an array of transducers 40 (or when using multiple applicators 18) at different power levels, which can remain fixed or themselves vary over time. Power level adjustments can be made without fundamental frequency adjustments, or in combination with fundamental frequency adjustments.

The parameters affecting power output take into account the output of the signal generator module 24; the physical dimensions and construction of the applicator 18; and the physiology of the tissue region to which ultrasonic energy is being applied. In the context of the illustrated embodiment, these parameters include the total output power ($P_{Total}$) (expressed in watts—W) provided to the transducer 40 by the signal generator module 24; the intensity of the power (expressed in watts per square centimeter—W/cm$^2$) in the effective radiating area of the applicator 18, which takes into account the total power $P_{Total}$ and the area of the material 48 overlaying the skirt 44; and the peak rarefactional acoustic pressure ($P_{Peak(Neg)}$) (expressed in Pascals—Pa) that the tissue experiences, which takes into consideration that the physiological tolerance of animal tissue to rarefactional pressure conditions is much less than its tolerance to compressional pressure conditions. $P_{Peak(Neg)}$ can be derived as a known function of W/cm$^2$.

In a preferred embodiment, the applicator 18 is sized to provide an intensity equal to or less than 3 W/cm$^2$ at a maximum total power output of equal to or less than 200 W (most preferably 15 W $\leq P_{Total} \leq$ 150 W) operating at a fundamental frequency of less than or equal to 500 kHz. Ultrasonic energy within the range of fundamental frequencies specified passes through bone, while also providing selectively different cavitational and mechanical effects (depending upon the frequency), and without substantial heating effects, as previously described. Power supplied within the total power output range specified meets the size, capacity, and cost requirements of battery power, to make a transportable, "follow the patient" treatment modality possible, as already described. Ultrasound intensity supplied within the power density range specified keeps peak rarefactional acoustic pressure within physiologically tolerable levels. The applicator 18 meeting these characteristics can therefore be beneficially used in conjunction with the transportable ultrasound generator machine 16, as described.

As stated above, the controller 26 can trigger the output according to time or a physiological event (such as ECG or respiration).

C. Pulsed Power Mode

The application of ultrasonic energy in a pulsed power mode can serve to reduce the localized heating effects that can arise due to operation of the transducer 40.

During the pulsed power mode, ultrasonic energy is applied at a desired fundamental frequency or within a desired range of fundamental frequencies at the prescribed power level or range of power levels (as described above, to achieve the desired physiologic effect) in a prescribed duty cycle (DC) (or range of duty cycles) and a prescribed pulse repetition frequency (PRF) (or range of pulse repetition frequencies).

The selection of the desired pulse repetition frequency (PRF) can be governed by practical reasons, e.g., to lay outside the human audible range, i.e., less than about 500 Hz. Desirably, the pulse repetition frequency (PRF) is between about 20 Hz to about 50 Hz (i.e, between about 20 pulses a second to about 50 pulses a second).

The duty cycle (DC) is equal to the pulse duration (PD) divided by one over the pulse repetition frequency (PRF). The pulse duration (PD) is the amount of time for one pulse. The pulse repetition frequency (PRF) represents the amount of time from the beginning of one pulse to the beginning of the next pulse. For example, given a pulse repetition frequency (PRF) of 30 Hz (30 pulses per second) and a duty cycle of 25% yields a pulse duration (PD) of approximately 8 msec. At these settings, the system outputs an 8 msec pulse followed by a 25 msec off period 30 times per second.

Given a pulse repetition frequency (PRF) selected at 27 Hz and a desired fundamental frequency of 27 kHz delivered in a power range of between about 15 to 20 watts, a duty cycle of about 50% or less meets the desired physiologic objectives in the thoracic cavity, with less incidence of localized conductive heating effects compared to a continuous application of the same fundamental frequency and power levels over a comparable period of time. Given these operating conditions, the duty cycle desirably lays in a range of between about 10% and about 25%.

D. Cooling

The controller 26 can also include a cooling function. During this function, the controller 26 causes an acoustic coupling media (e.g., water or saline or another fluid or gel) to circulate at or near the ultrasound applicator 18. The circulation of the acoustic coupling media conducts heat that may arise during the formation and application of ultrasonic energy.

Figure 14:
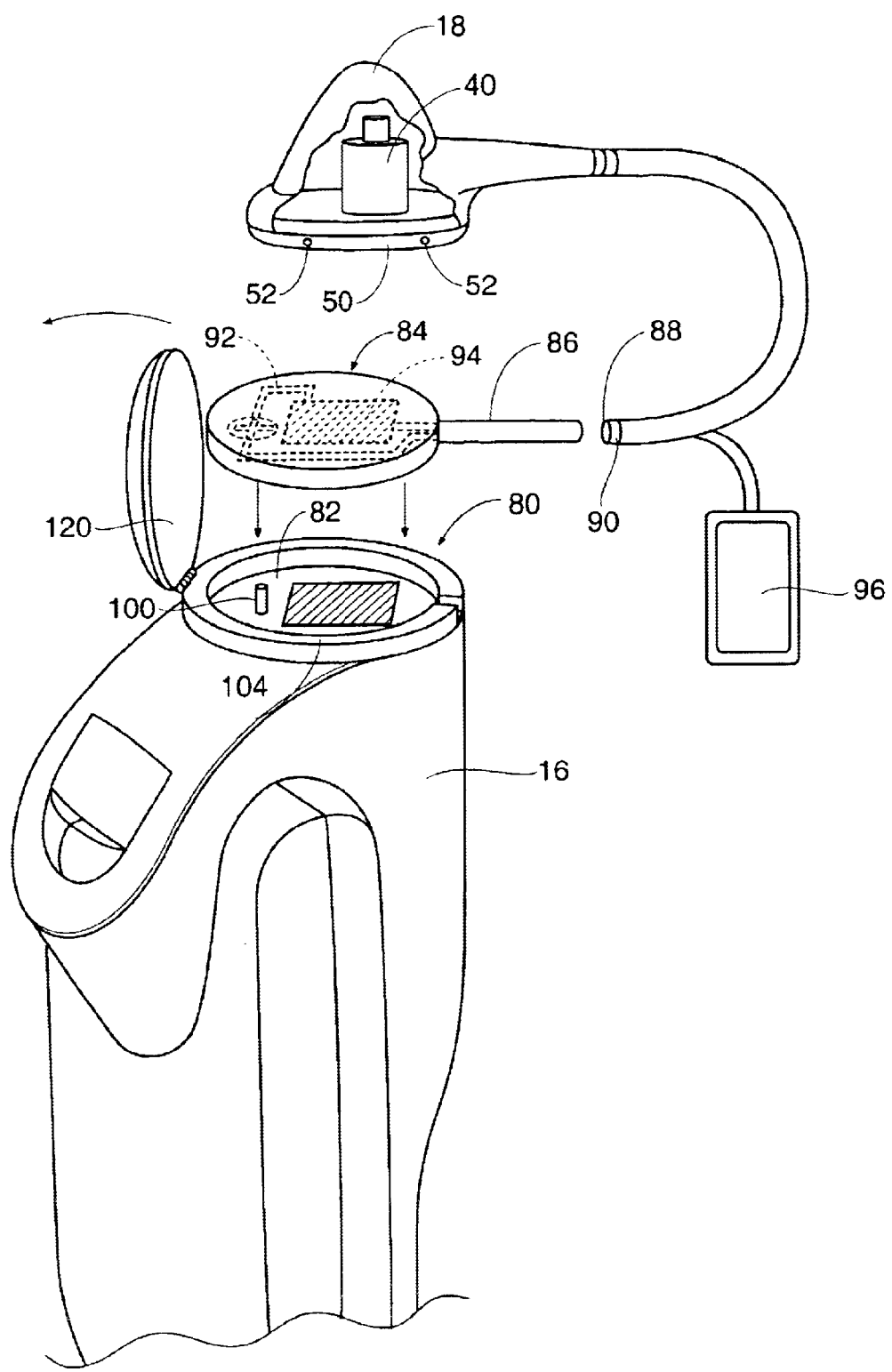
FIG. 14 is a perspective view of a cooling module and associated heat exchange cassette that the system shown in FIG. 1 can incorporate.

In one embodiment, the machine 16 carries out this function using a acoustic coupling media handling module 80 on the machine 16 (see FIG. 14). The module 80 operatively engages a pumping and heat exchange cassette 84 coupled to the applicator 18.

In the embodiment shown in FIG. 14, the module 80 is physically located within a cavity 82 formed in the machine 16. Access to the cavity 82 is governed by a hinged door 120 (shown closed in FIG. 1 and opened in FIG. 14). The cassette 84 is received in the cavity 82 when the door 120 is opened and enclosed within the cavity 82 for use when the door 120 is subsequently closed. Opening the door 120 after use allows the operator to remove and dispose of the cassette 84.

Alternatively, the cavity 82 can be free of a closure door 120, and the cassette 82 directly plugs into the cavity 82. In this arrangement, the top surface of the cassette 84 serves as a closure lid.

In the illustrated embodiment (see FIG. 14), the cassette 84 comprises a molded plastic assembly that is integrally connected by tubing 86 to the applicator 18. In this arrangement, the cassette 84 forms a pre-connected unit of the disposable components of the system 10. Alternatively, the cassette 84 and tubing 86 could form a separate component that is connected to the applicator 18 at time of use. In this arrangement, the cassette 84 and tubing 86 still preferably comprise a single use, disposable unit.

Figure 15:
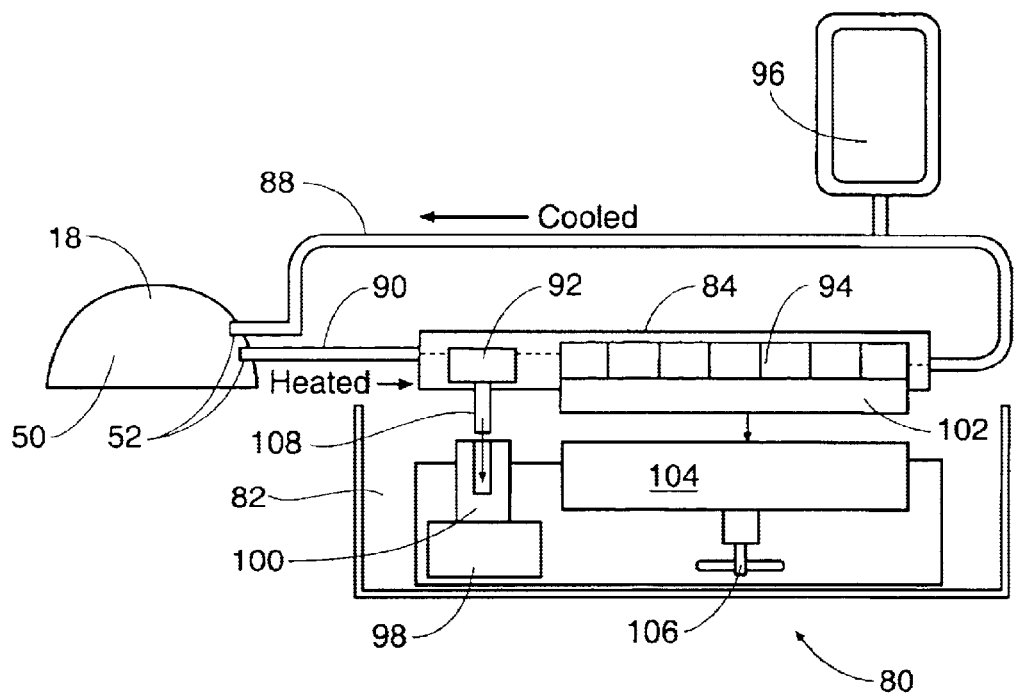
FIG. 15 is a side schematic view of the cooling module and heat exchange cassette shown in FIG. 14.

In the illustrated embodiment, the tubing 86 includes two media flow lumens 88 and 90 (although individual tubing lengths can also be used). In the embodiment shown in FIG. 14, the cassette 84 includes an internal pumping mechanism 92, such as a diaphragm pump or centrifugal pump. FIG. 15 also diagrammatically shows this arrangement.

The cassette 84 also includes an internal heat exchange circuit 94 coupled to the pumping mechanism 92. The pumping mechanism 92, when operated, circulates media through the lumens 88 and 90 and the heat exchange circuit 94. Media is thereby circulated by the pumping mechanism 92 in a closed loop from the cassette 84 through the lumen 88 and into the bladder chamber 50 of the applicator 18 (through one of the ports 52), where heat generated by operation of the transducer 40 is conducted into the media. The heated media is withdrawn by the pumping mechanism 92 from the bladder chamber 50 through the other lumen 90 (through the other port 52) into the cassette 84. Preformed interior media paths in the cassette 84 direct the media through the heat exchange circuit 94, where heat is conducted from the media.

The circulating media can be supplied by a bag 96 that is coupled to the tubing 86 at time of use or, alternatively, that is integrally connected to the cassette during manufacture. Still alternatively, the media channels of the cassette 84 and the tubing 86 can be charged with media during manufacture.

In this arrangement (see, in particular, FIG. 15), the module 80 includes an internal electric motor 98 having a drive shaft 100. The motor drive shaft 100 is keyed to operatively engage the driver 108 of the pumping mechanism 92 when the cassette 84 is fitted into the cavity 82. Operation of the motor 98 drives the pumping mechanism 92 to circulate media to cool the applicator 18.

Also in the illustrated embodiment (see FIG. 15), the cassette 84 includes an externally exposed heat conducting plate 102. The plate 102 is coupled in heat conducting association with the heat exchange circuit 94. When the cassette 84 is fitted within the cavity 82 of the module 80, the heat conducting plate 102 on the cassette 84 contacts a heat conducting plate 104 in the module 80. The plate 104 is cooled by an interior fan 106 in the module 80, to withdraw heat from the heat exchange circuit 94 of the cassette 84. In this way, media is cooled as it circulates through the cassette.

In the embodiment shown in FIG. 15, no media circulates within the module 80 itself. The closed loop flow of media is all external to the machine 16.

Figure 16:
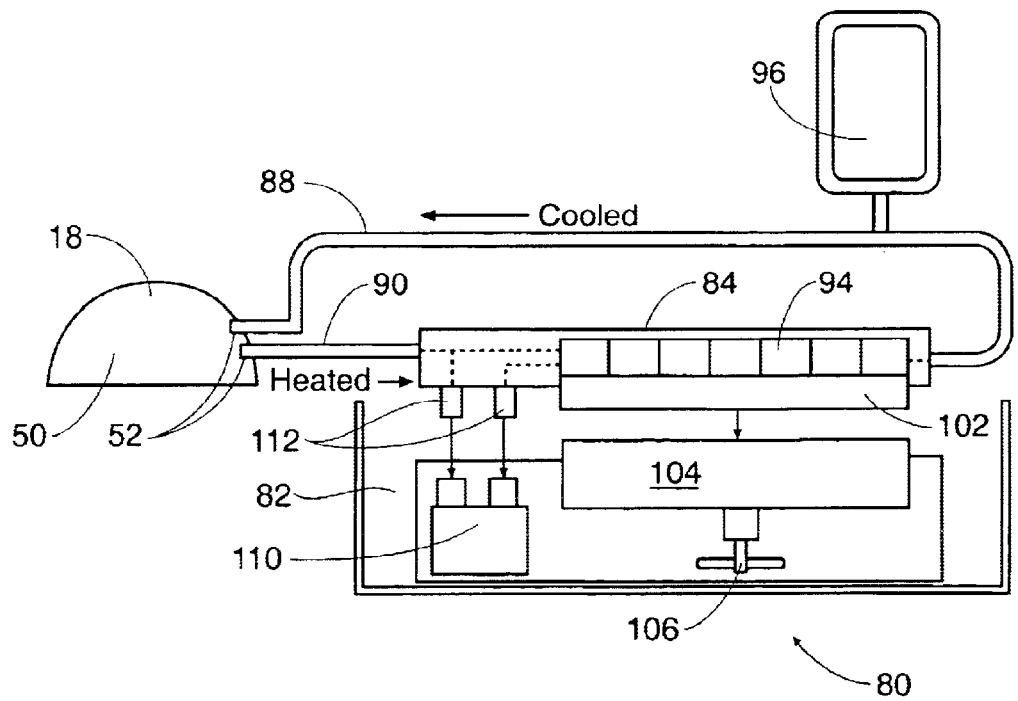
FIG. 16 is a side schematic view of another embodiment of a cooling module and heat exchange cassette that the system shown in FIG. 1 can incorporate.

In an alternative arrangement (see FIG. 16), the cassette 84 does not include an on-board pumping mechanism.

Instead, the module 80 includes an interior pump 110 that couples to ports 112 that communicate with the interior media paths of the cassette 84. In this arrangement, the pump 110 conveys media into and through the module 84 to circulate media through the heat exchanger circuit 94 of the cassette 84 in the manner previously described.

Other arrangements are also possible. For example, the cooling function can be implemented by a conventional peristaltic pump head mounted outside the chassis 22. The pump head couples to external tubing coupled to the applicator 18 to circulate media through the cassette. Still alternatively, the media handling module 80 can comprise a separate unit that can be remotely coupled to the machine 16 when cooling is desired.

Alternatively, the cassette can communicate with a separate bladder placed about the applicator 18 to achieve localized cooling.

E. Maintaining Acoustic Output

Acoustic output of the system can be maintained by sensing one or more system parameters, comparing the sensed parameters to a desired level, and adjusting the system to maintain the desired level. For example, a system parameter that can be sensed is impedance. Based upon the impedance level, the controller 26 operates the acoustic coupling media handling module 80 to achieve an ultrasonic energy control function; namely, by maintaining the impedance and thus the acoustic output (AO) of the transducer 40 essentially constant at the fundamental frequency applied.

Figure 17:
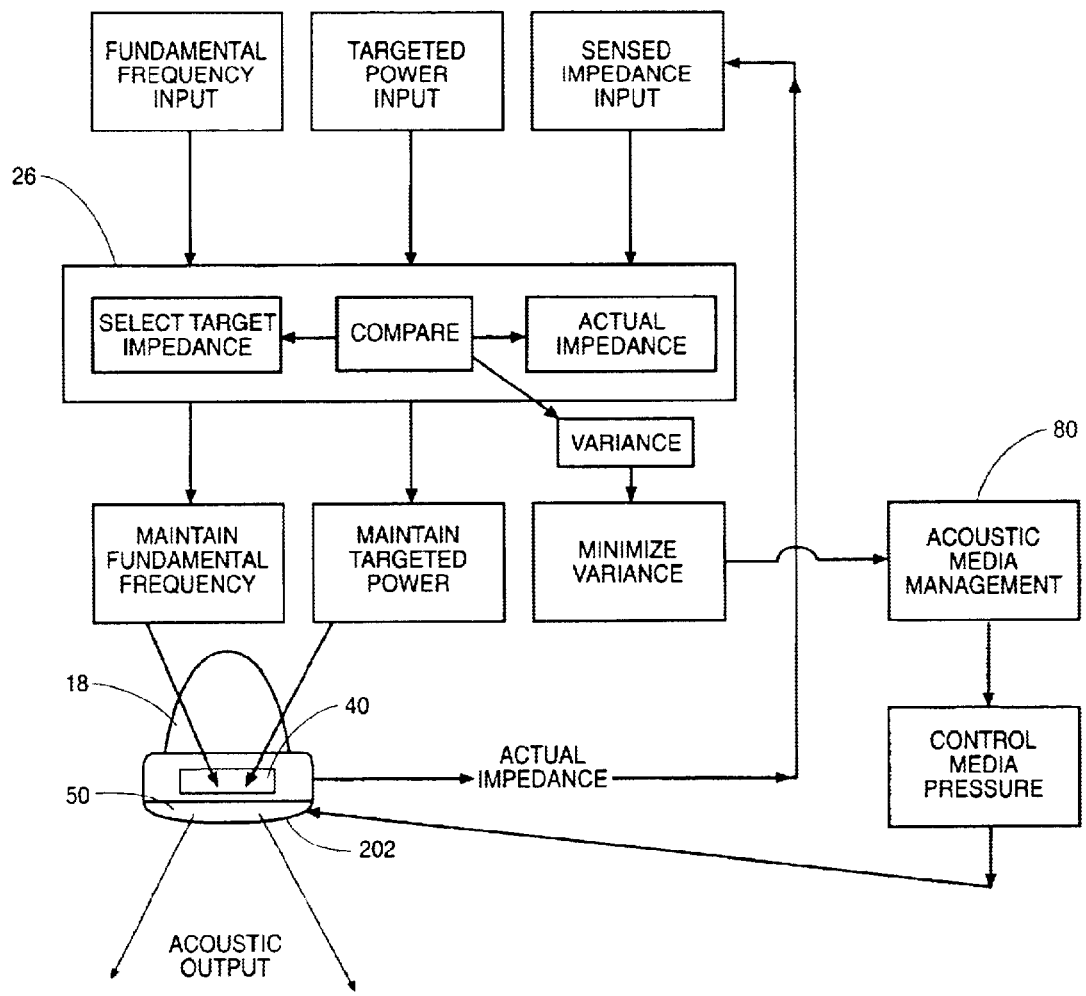
FIG. 17 is a schematic view of a controller that can be used in conjunction with the system shown in FIG. 1, which combines power control and media management control to maintain an essentially constant acoustic output for the ultrasound applicator.
Figure 18:
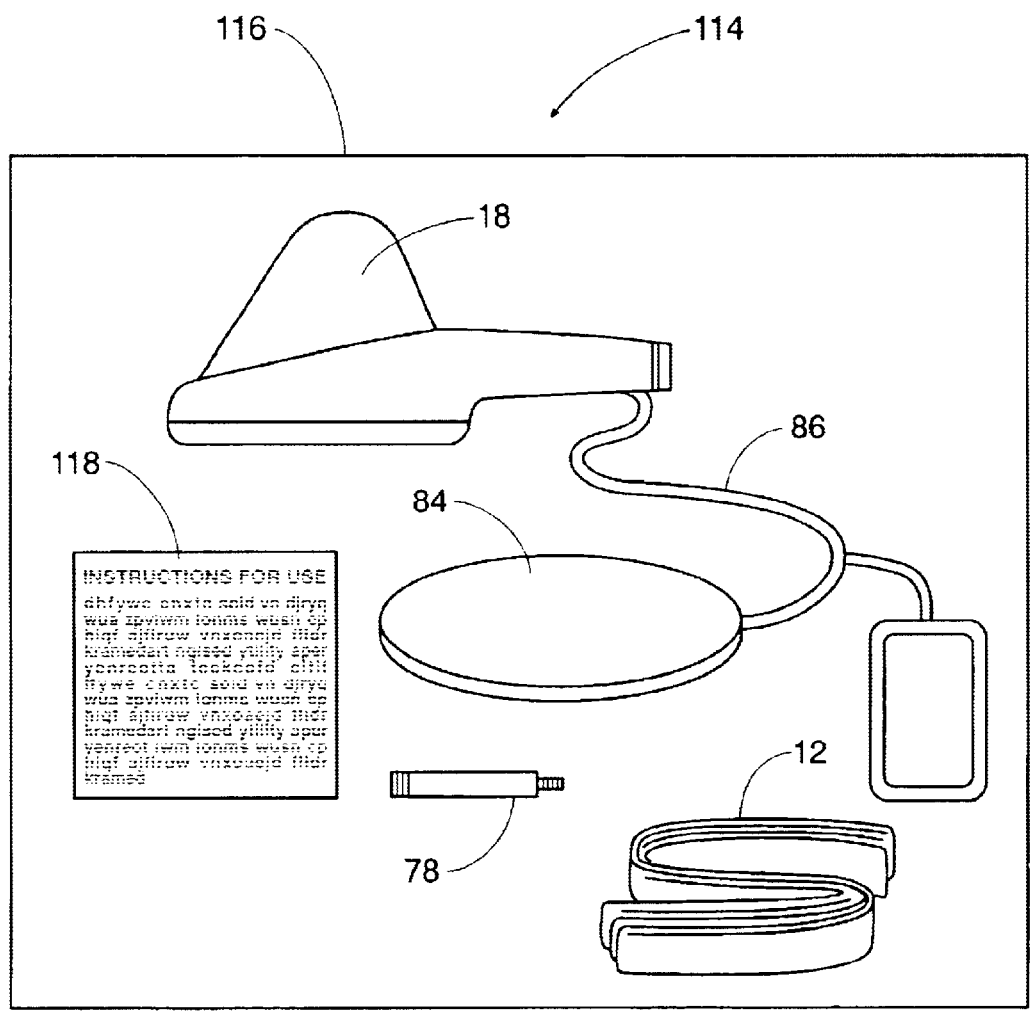
FIG. 18 is a plan view of a kit, in which all or some of the disposable components of the system shown in FIG. 1 can be packaged before use, along with instructions for using the components to achieve the features of the invention.

For instance, for a given power output, there is a desired range of impedance values. As FIG. 17 shows, the controller 26 receives as input from the operator the fundamental frequency selected for operation. The controller 26 determines, e.g., through preprogrammed logic or look-up tables, what the corresponding impedance value or range of values are.

As FIG. 17 also shows, the controller 26 also receives as input a targeted power (P) at which the selected fundamental frequency is to be applied. Knowing targeted power (P) and impedance (IMP) for the selected fundamental frequency, the controller 26 derives a targeted acoustic output (AO). The controller 26 operates to maintain the targeted acoustic output essentially constant during operation.

Under control of the controller 26, the transducer 40 outputs acoustic energy. The transducer also senses actual impedance, which the controller 26 receives an input.

The controller 26 periodically compares the sensed actual impedance to the targeted minimum impedance. If the sensed actual impedance varies from the targeted minimum impedance, the controller 26 commands operation of the media handling module 80 to adjust pressure within the bladder 50 to minimize the variance. In this way, the controller 26 is able to maintain an essentially constant acoustic output at an essentially constant electrical output, without direct sensing of acoustic output. The controller 26 can, if desired, adjust electrical output to maintain an essentially constant acoustic output, as the variance is eliminated and the impedance returns to the desired target minimum value.

F. Monitoring and Displaying Output

The controller 26 can implement various output monitoring and feedback control schemes. For example, the controller 26 can monitor ultrasonic output by employing one or more accelerometers 78 (see FIG. 3) (or other types of displacement or compression feedback components) on or within the applicator 18. The ultrasonic output that is monitored in this way can comprise fundamental frequency, total power output, power density, acoustic pressure, or Mechanical Index (MI). The controller 26 can also monitor temperature conditions using one or more temperature sensors 140 or thermistors on the applicator 18.

Implementing feedback control schemes, the controller 26 can also execute various auto-calibration schemes. The controller 26 can also implement feedback control to achieve various auto-optimization schemes, e.g., in which power, fundamental frequency, and/or acoustic pressure outputs are monitored and optimized according to prescribed criteria to meet the desired treatment objectives and outcomes.

The controller 26 can also implement schemes to identify the nature and type of applicator when coupled to the machine. These schemes can also include functions that register and identify applicators that have undergone a prior use, to monitor and, if desired, prevent reuse, store treatment data, and provide serial number identification. This function can be accomplished using, e.g., analog electrical elements (e.g., a capacitor or resistor) and/or solid state elements (micro-chip, ROM, EEROM, EPROM, or non volatile RAM) within the applicator 18 and/or in the controller 26.

The controller 26 can also display the output in various text or graphical fields on the operator interface 28. For example, the controller 26 can conveniently display on the interface a timer, showing the time of treatment; a power ON indicator; a cooling ON indicator; and ultrasonics ON indicator; and other data reflecting information helpful to the operator, for example, the temperature, fundamental frequency, the total power output, the power density, the acoustic pressure, and/or Mechanical Index.

The controller 26 can also include an internal or external input device to allow the operator to input information (e.g., the patient's name and other identification) pertaining to the treatment session. The controller 26 can also include an internal or external storage device to allow storage of this information for output to a disk or a printer in a desired format, e.g., along with operating parameters such as acoustical intensity, treatment duration, etc.

The controller 26 can also provide the means to link the machine 16 at the treatment location in communication with one or more remote locations via, e.g., cellular networks, digital networks, modem, Internet, or satellites.

V. Integrated Function

The machine 16 and associated applicator 18 can form a part of a free standing system 10, as the previous drawings demonstrate. The machine 16 can also be integrated into another functional device, such as an ECG apparatus, a defibrillator apparatus, a diagnostic ultrasound apparatus, or another other diagnostic or therapeutic apparatus. In this arrangement, the former functionality of the diagnostic or therapeutic device is augmented by the added ability to provide noninvasive ultrasound-induced increased blood perfusion and/or thrombolysis.

VI. Supplying the System

As before explained, the machine 16 is intended to be a durable item capable of multiple uses.

One or more of the disposable components of the system 10, which are intended for single use, can be separately supplied in a kit 114. For example, in one embodiment (see FIG. 12), the kit 114 can include, contained within in a sealed, tear-apart package 116, the applicator 18 and instructions 118 for using the applicator 18 in association with the machine 16 to transcutaneously apply ultrasonic energy to enhance blood perfusion. In this regard, the instructions 118 may set forth all or some of the method steps, described above. The instructions 118 may also comprise the method steps to transcutaneously apply ultrasonic energy in association with the administration of a thrombolytic agent.

Additional elements may also be provided with the applicator 18 in the kit 114, such as the patient stabilization assembly 12, the heat exchanging cassette 84 and associated tubing 86, and exterior ultrasound conducting material 78. These and other additional elements may also be packaged separately.

The instructions 118 can comprise printed materials. Alternatively, the instructions 118 can comprise a recorded disk or media containing computer readable data or images, a video tape, a sound recording, and like material.

Various features of the invention are set forth in the following claims.

We claim:

1. A system for applying ultrasound energy to a body region comprising an ultrasound applicator including a housing, an ultrasound transducer carried by the housing, and a chamber sized to hold an acoustic coupling media subject to a pressure in acoustic communication with the ultrasound transducer, an acoustic coupling media handling module communicating with the chamber to selectively vary the pressure within the chamber, an electrical signal generating machine adapted to be coupled to the ultrasound transducer, and a controller coupled to the electrical signal generating machine to generate electrical signals to operate the ultrasound transducer to output acoustic energy at a selected intensity level, the controller including a function to sense at least one system parameter and compare the sensed system parameter to a desired level, the controller also being coupled to the acoustic coupling media handling module to command variations in the pressure in the chamber based, at least in part, upon the comparison.

2. A system according to claim 1
wherein the system parameter includes impedance.

3. A system according to claim 2
wherein the controller commands variation in the pressure in the chamber based, at least in part, upon variance between the sensed impedance and a desired impedance level.

4. A system according to claim 1
wherein the controller includes a function that selects the desired level based upon the selected intensity level.

5. A system according to claim 1
wherein the controller commands variation in the pressure in the chamber to maintain an essentially constant acoustic output.

6. A system according to claim 1
wherein the acoustic coupling media within the chamber conducts heat from the ultrasound transducer.

7. A system according to claim 1
wherein the chamber includes an ultrasound coupling surface that, in use, contacts skin overlaying the body region.

8. A system according to claim 7
wherein the ultrasound coupling surface includes a flexible material that forms a contour-conforming interface with skin.

9. A method for applying ultrasound energy to a body region comprising the steps of providing an ultrasound applicator including a housing, an ultrasound transducer carried by the housing, and a chamber sized to hold an acoustic coupling media subject to a pressure in acoustic communication with the ultrasound transducer, generating electrical signals to operate the ultrasound transducer to output acoustic energy at a selected intensity level, sensing at least one system parameter and comparing the sensed system parameter to a desired level, and varying the pressure in the chamber based, at least in part, upon the comparison.

10. A method according to claim 9
wherein the system parameter includes impedance.

11. A method according to claim 10
wherein the pressure is varied in the chamber based, at least in part, upon variance between the sensed impedance and a desired impedance level.

12. A method according to claim 9
further including selecting the desired level based upon the selected intensity level.

13. A method according to claim 9
wherein the pressure is varied in the chamber to maintain an essentially constant acoustic output.

14. A method according to claim 9
wherein the acoustic coupling media within the chamber conducts heat from the ultrasound transducer.

* * * * *

UNITED STATES PATENT AND TRADEMARK OFFICE
CERTIFICATE OF CORRECTION

PATENT NO.         : 6,790,187 B2                                          Page 1 of 1
APPLICATION NO. : 09/938308
DATED              : September 14, 2004
INVENTOR(S)        : Todd A. Thompson, Veijo Suorsa and Michael J. Horzewski It is certified that error appears in the above-identified patent and that said Letters Patent is hereby corrected as shown below:

On the Title of the issued patent under (item 75) "Inventors" delete "Howzewski" and insert -- Horzewski --

Signed and Sealed this

Twenty-fourth Day of April, 2007

JON W. DUDAS
*Director of the United States Patent and Trademark Office*